United States Patent
Nahm et al.

(10) Patent No.: US 10,274,473 B2
(45) Date of Patent: Apr. 30, 2019

(54) SENSOR

(71) Applicant: KOREA RESEARCH INSTITUTE OF STANDARDS AND SCIENCE, Daejeon (KR)

(72) Inventors: SeungHoon Nahm, Daejeon (KR); Un Bong Baek, Daejeon (KR); Seok Cheol Lee, Daejeon (KR); InHyun Cheong, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 15/300,514

(22) PCT Filed: Mar. 17, 2015

(86) PCT No.: PCT/KR2015/002583
§ 371 (c)(1),
(2) Date: Sep. 29, 2016

(87) PCT Pub. No.: WO2015/152538
PCT Pub. Date: Oct. 8, 2015

(65) Prior Publication Data
US 2017/0184557 A1    Jun. 29, 2017

(30) Foreign Application Priority Data
Mar. 31, 2014  (KR) .................. 10-2014-0037555

(51) Int. Cl.
*G01N 27/12* (2006.01)
*G01N 33/00* (2006.01)

(52) U.S. Cl.
CPC ......... *G01N 33/005* (2013.01); *G01N 27/125* (2013.01); *G01N 27/127* (2013.01)

(58) Field of Classification Search
CPC .................... G01N 33/005; G01N 27/125
See application file for complete search history.

(56) References Cited

U.S. PATENT DOCUMENTS 1,860,544 A * 5/1932 Krueger ............... G01N 27/185
73/25.03
2010/0025241 A1    2/2010 Hane et al.
(Continued)

FOREIGN PATENT DOCUMENTS

JP          5042010 B2    10/2012
KR    20010010089 A     2/2001
(Continued)

OTHER PUBLICATIONS

Lange, Ulrich, et al. "Hydrogen sensor based on a graphene-palladium nanocomposite." Electrochimica Acta 56.10 (2011): 3707-3712.*

(Continued)

*Primary Examiner* — Robert J Eom
(74) *Attorney, Agent, or Firm* — Harness, Dickey & Pierce, P.L.C.

(57) ABSTRACT

The present invention relates to a sensor for sensing hydrogen. The sensor of the present invention comprises: a core which reacts with hydrogen to change a resistance value; at least two electrodes connected to the core; and a variable resistor which is connected to at least one of the two electrodes and of which the resistance value changes in response to a control signal, wherein the core includes palladium having a thin film shape, and graphene which is applied on the palladium and has a thin film shape.

13 Claims, 5 Drawing Sheets

(56) References Cited

U.S. PATENT DOCUMENTS

2010/0326825 A1    12/2010  Hane et al.
2011/0088931 A1*   4/2011   Lettow .................. B82Y 30/00
                                                    174/257

FOREIGN PATENT DOCUMENTS

| KR | 100959245 B1 | 5/2010 |
| KR | 101304340 B1 | 9/2013 |
| KR | 101408105 B1 | 6/2014 |
| KR | 101463958 B1 | 12/2014 |

OTHER PUBLICATIONS

International Search Report PCT/ISA/210 for International Application No. PCT/KR2015/002583 dated Mar. 17, 2015.
Min Gyun Chung et al. "Flexible Hydrogen Sensors Using Graphene with Palladium Nanoparticle Decoration". Sensors and Actuators B: Chemical 169. Elsevier B.V. (2012). pp. 387-392.

* cited by examiner (210)

(220)

(230)

(240)

(250)

(310)

(320)

(330)

(340)

(350)

SENSOR

CROSS-REFERENCE TO RELATED APPLICATIONS

This application is a national phase under 35 U.S.C. § 371 of PCT International Application No. PCT/KR2015/002583 which has an International filing date of Mar. 17, 2015, which claims priority to Korean Application No. 10-2014-0037555, filed Mar. 31, 2014, the entire contents of each of which are hereby incorporated by reference.

TECHNICAL FIELD

The present invention relates to a sensor, and more particularly, to a sensor capable of sensing hydrogen at a low cost.

BACKGROUND ART

In order to solve environmental pollution problems including global warming due to fossil fuel usage and an energy shortage phenomenon due to fossil fuel depletion, various alternative energy are being researched. As one of the alternative energy, a study on hydrogen is being accelerated.

The hydrogen energy may have an advantage solving all the above-described two problems and be obtained from water abundantly distributed in the earth. Also, the hydrogen energy may overcome the finitude of the conventional fossil fuel as an energy source capable of being recycled into the water when the use thereof is completed. Furthermore, the hydrogen may not generate pollutants except for an extremely small amount of $NO_x$. Thus, the development of the hydrogen energy is being accelerated in recent years to solve the energy resource depletion and the environmental pollution problems at the same time. Accordingly, the hydrogen energy is expected to be widely used.

However, the hydrogen gas may have a risk of explosion when the hydrogen gas of 4% to 75% or more leaks into the atmosphere. Thus, the hydrogen gas is hard to be applied as the hydrogen energy source in hydrogen fuel for home and a hydrogen fuel cell vehicle unless an accurate and stable management is secured. Thus, needs for hydrogen sensors, which are capable of early detecting the leakage of hydrogen, are being on the rise.

Sensors using catalyzed combustion or a heating wire and semiconductor sensors using silicon dioxide ($SiO_2$), aluminum nitride (AlN), and metal oxide (nitride) are being developed as the hydrogen sensors. However, the above-described sensors have not only large sizes and complex structures, but also have a high cost.

DISCLOSURE OF THE INVENTION

Technical Problem

An object of the present invention is to provide a sensor which is capable of sensing hydrogen at a low cost.

Another object of the present invention is to provide a sensor capable of being miniaturized and sensing hydrogen through a simple structure.

Technical Solution

A sensor according to the present invention include: a core which reacts with hydrogen to change in resistance value; at least two electrodes connected to the core; and a variable resistor connected to one of the at least two electrodes and having a resistance value that changes in response to a control signal, wherein the core comprising: palladium having a thin film shape; and graphene applied on the palladium and having a thin film shape.

In an embodiment, the graphene may have a thickness greater by N times than that of the palladium (where the N is a natural number).

In an embodiment, the N may have a value of 7.

In an embodiment, the graphene may be formed in a piezoelectric manner through applying of a graphene solution so as to have the thin film shape.

In an embodiment, the palladium may be formed in a piezoelectric manner through applying of a palladium solution so as to have the thin film shape.

In an embodiment, the variable resistor may apply an offset resistance value to a variation in resistance value of the core in response to the control signal.

In an embodiment, the sensor may further include: a housing for protecting the core and the at least two electrodes; and a fixing member inserted to the housing to fix the core and the at least two electrodes.

Advantageous Effects

The sensor of the present invention may use the core using the palladium and graphene having the thin film shape to sense the hydrogen at a low cost. In addition, the sensor of the present invention may be miniaturized by using the miniaturized core and sense the hydrogen through the simple structure.

BEST MODE FOR CARRYING OUT THE INVENTION

Figure 1:
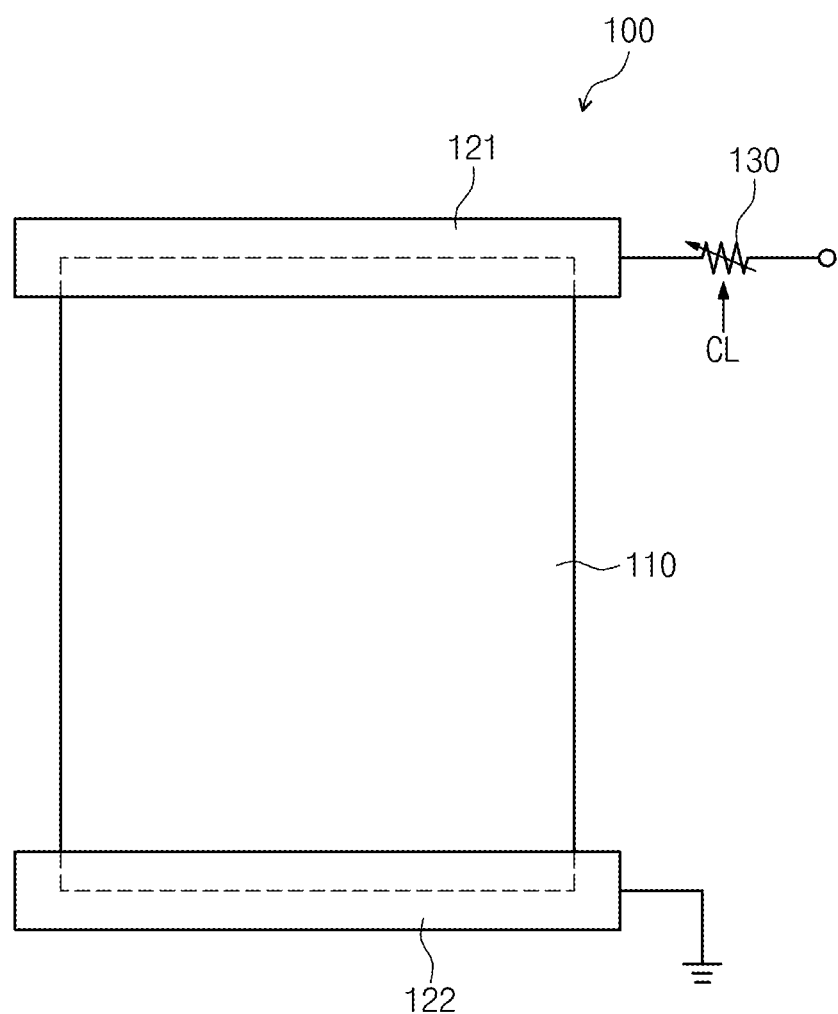
FIG. 1 is a drawing illustrating an example of a structure of a sensor for sensing hydrogen.

FIG. 1 is a drawing illustrating a best mode for embodying the present invention.

MODE FOR CARRYING OUT THE INVENTION

Hereinafter, a preferred embodiment according to the present invention will be described in more detail with reference to the accompanying drawings. In the following description, only necessary elements to understand an operation according to the present invention are explained, and it is noted that description of other elements will be omitted not to obscure subject matters of the present invention.

The present invention provides a sensor capable of being manufactured at a low cost.

FIG. 1 is a drawing illustrating an example of a structure of a sensor for sensing hydrogen.

Referring to FIG. 1, a sensor 100 includes a core 110, electrodes 121 and 122, a variable resistor 130.

The core 110 includes a thin film-type palladium (Pd) and a thin film-type graphene. Here, the core 110 has a structure in which graphene is applied (or printed) at least one time on a top surface of palladium applied (or printed) in the form of a thin film. The core 110 reacts with hydrogen to change a resistance value.

The electrodes 121 and 122 are coupled to the core 110 to measure a variation in resistance value of the core 110. Here, although two electrodes 121 and 122 are provided as an example, the various numbers of electrodes may be provided.

The first electrode 121 is connected to the variable resistor 130, and the second electrode 122 is connected to a ground terminal.

The variable resistor 130 may have an offset resistance value changing in response to an external control signal CL. The variable resistor 130 may apply the offset resistance value to the resistance value of the core 110 so as to accurately measure the resistance value from the core 110. The variable resistor 130 may have, for example, a resistance value of about 1 kilo-ohm (kΩ) and may be set to a value ranging from about 0 to about 10 kΩ.

As described above, the hydrogen sensor 100 includes the core 110 having a structure in which the palladium and graphene, which have a thin film or film shape, are coupled to each other. The core 110 is formed through an operation of sequentially printing a palladium solution and a graphene solution. As a result, the core 110 used in the sensor 110 decreases in manufacturing costs to implement the sensor 100 for sensing hydrogen at a low cost.

Also, the sensor 100 may be miniaturized as the core 100 is capable of being manufactured to have a size of 10 millimeters (mm) or less (for example, several millimeters (mm) or several micrometers (m)) and may have a simple structure as being constituted by the core 110, the electrodes 121 and 122, and the variable resistor 130.

Figure 2:
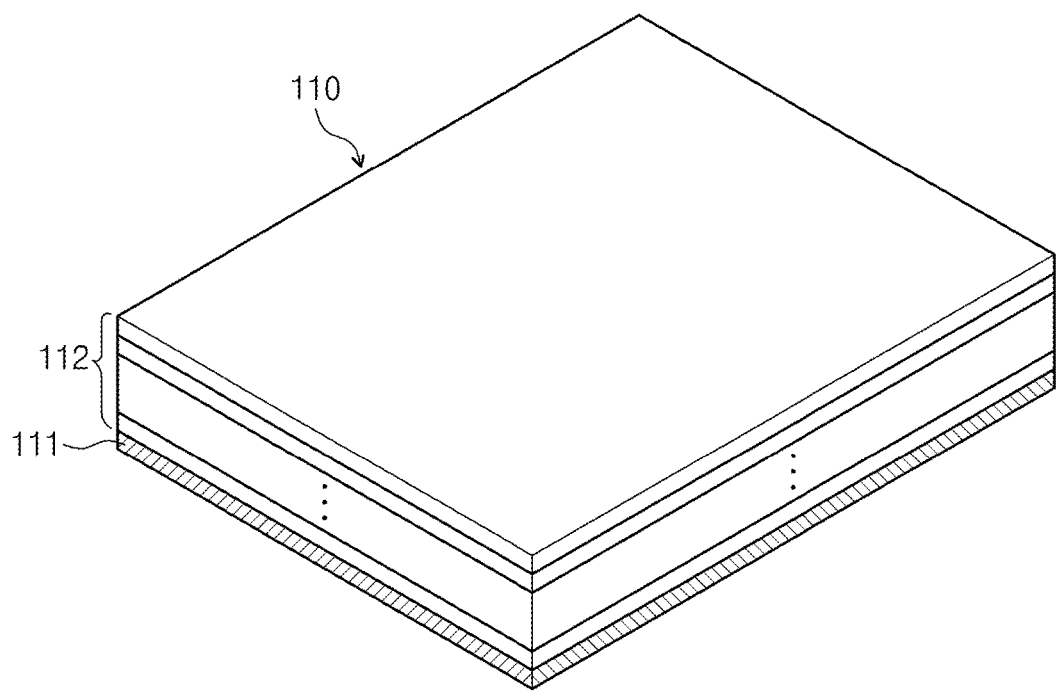
FIG. 2 is a drawing illustrating an example of a side surface of a core illustrated in FIG. 1.

FIG. 2 is a diagram illustrating an example of a side surface of the core of FIG. 1.

Referring to FIG. 2, the core 110 may be implemented in the thin film shape through application (or printing) using a device such as a printer. Here, the palladium 111 is disposed at a lower portion of the core 110, and the graphene 112 is disposed on the top surface of the palladium 111.

The palladium 111 serves as a catalyst to attract the hydrogen through molecular binding induction. Also, the graphene 112 has a function of changing a resistance value by the hydrogen coupled through the palladium 111.

In the sensor 100, the core 110 may be constituted by using the palladium 111 and the graphene 112 having the above-described functions.

When the core 110 is formed, a printing paper or a film paper, and the like may be utilized for applying the palladium solution. First, the palladium solution is applied one time on the film paper and the like to form the palladium 111 having the thin film shape. Then, the graphene solution may be applied several times on the surface of the palladium 111 through the printing operation. Here, the graphene 112 may have a thickness greater by N times (for example, N is a natural number) than that of the palladium 111 on the basis of the number of operations of applying the graphene solution on the top surface of the palladium 111.

Here, it is described that the graphene is applied on the top surface of the palladium 111. On the other hand, the palladium may be applied on the top surface of the graphene after the graphene solution is completely applied. Here, the palladium 111 is disposed on the top surface of the graphene 112.

Figure 3:
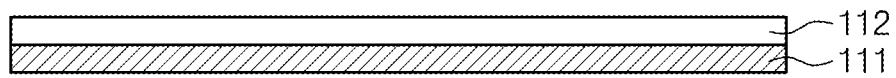
FIG. 3 is a drawing illustrating various thicknesses of the core illustrated in FIG. 1.
Figure 3:
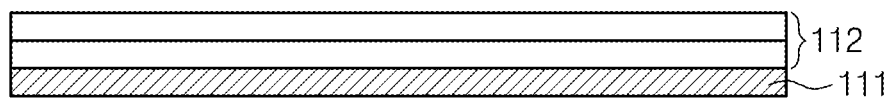
Figure 3:
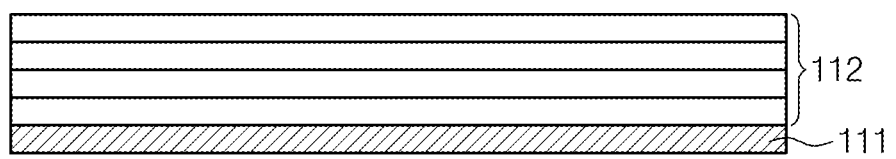
Figure 3:
Figure 3:
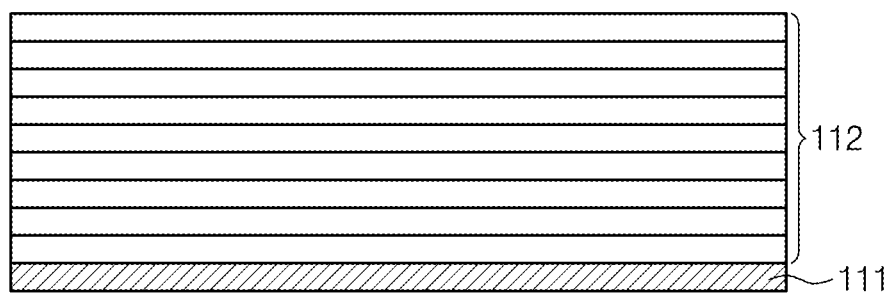

FIG. 3 is a diagram illustrating various thicknesses of the core of FIG. 1.

Referring to FIG. 3, in the core 110, the graphene 112 may be formed with various thicknesses according to the number of operations of applying the graphene solution on the top surface of the palladium 111.

In a cross-sectional view 210 of FIG. 3, the graphene solution is applied one time on the top surface of the palladium 111. Here, the palladium 111 may be formed in the same thickness as the graphene 112.

In a cross-sectional view 220 of FIG. 3, the graphene solution is applied two times on the top surface of the palladium 111. Here, the palladium 111 may have a thickness greater by two times than that of the graphene 112.

In a cross-sectional view 230 of FIG. 3, the graphene solution is applied four times on the top surface of the palladium 111. Here, the palladium 111 may have a thickness greater by four times than that of the graphene 112.

In a cross-sectional view 240 of FIG. 3, the graphene solution is applied seven times on the top surface of the palladium 111. Here, the palladium 111 may have a thickness greater by seven times than that of the graphene 112.

In a cross-sectional view 250 of FIG. 3, the graphene solution is applied nine times on the top surface of the palladium 111. Here, the palladium 111 may have a thickness greater by nine times than that of the graphene 112.

FIG. 3 illustrated as an example in which the graphene 112 is formed on the top surface of the palladium 111 to have a thickness greater by N times than that of the palladium 111. Alternatively, the graphene 112 may be set to have various thicknesses in addition to the above-described thickness differences.

Also, the difference in thickness of the palladium 111 and the graphene 112 causes various changes of a performance. Thus, the core having a thickness that is capable of realizing suitable performance according to performance required for the sensor 100 may be used.

For example, the sensor 100 may use the core 110 constituted by the graphene 112, which has a thickness greater by seven times than that of the palladium 111 (1Pd7G).

However, when the printing operation is performed, the palladium 111 or the graphene 112 may be changed in thickness according to the application of the solution. In this case, the number of applying operations according to the manufacturing of the core 110 may be changed through the variation in thickness, and the difference in thickness of the palladium 111 and the graphene 112 may be set to have a multiple of a real number, but a natural number.

Figure 4:
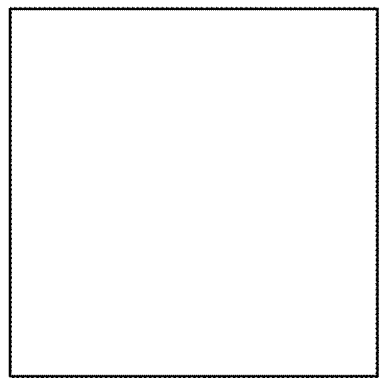
FIG. 4 is a drawing illustrating an example of various shapes of the core illustrated in FIG. 1.
Figure 4:
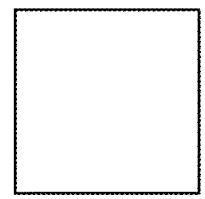
Figure 4:
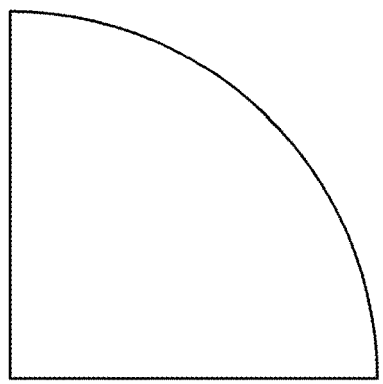
Figure 4:
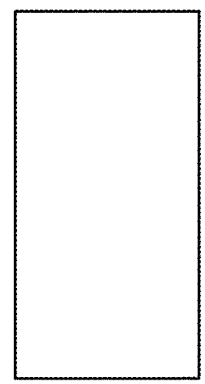
Figure 4:
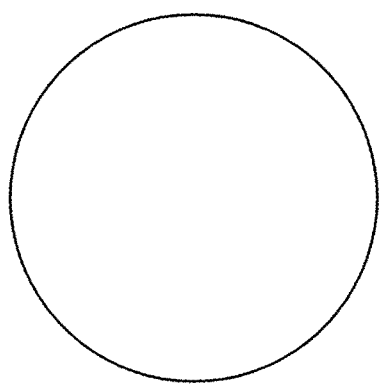

FIG. 4 is a diagram illustrating an example of various shapes of the core illustrated in FIG. 1.

Referring to FIG. 4, the core 110 obtained by the printing operation and the like may change in size and shape.

In plan views 310 and 320 of FIG. 4, the core may have a square shape. Here, the cores may be formed to have sizes different from each other in spite of the same shapes as those in the views 310 and 320.

In a plan view 330 of FIG. 4, the core may have a fan shape.

In a plan view 340 of FIG. 4, the core may have a rectangular shape.

In a plan view 350 of FIG. 4, the core may have a circular shape.

The shapes of the core may be merely an example, and thus, the core may have various shapes according to the sizes and shapes of the sensor 100 in addition to the above-described shapes.

Figure 5:
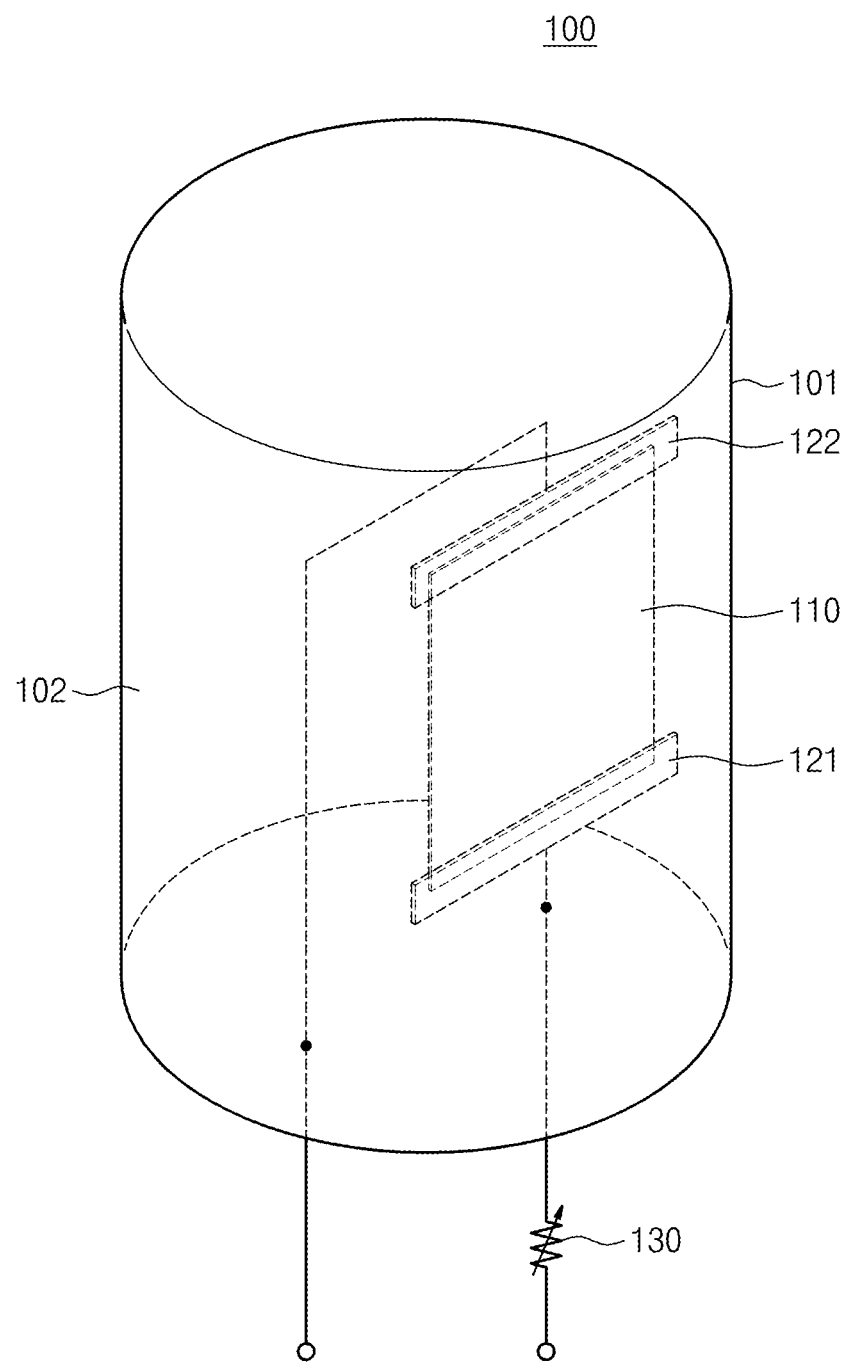
FIG. 5 is a drawing illustrating an example of a module including the sensor for sensing the hydrogen, which is illustrated in FIG. 1.

FIG. 5 is a diagram illustrating an example of a module including the sensor sensing hydrogen illustrated in FIG. 1.

Referring to FIG. 5, the sensor 100 includes a housing 101, a fixing member 102, a core 110, electrodes 121 and 122, and a variable resistor 130.

The core 110 and the electrodes 121 and 122 are disposed in the housing 101 in order to protect the sensor 100. The fixing member 102 is provided in the housing 101 to fix the core 110 and the electrodes 121 and 122. The fixing member 102 includes a non-metal material such as cotton.

Also, the variable resistor 130 is connected to the electrode 121.

Thus, the sensor for sensing the hydrogen may use the core manufactured in the simple printing manner and thus be produced at a low cost. Furthermore, since the sensor decreases in price, several sensors may be used at the same cost when compared to the existing sensor in a situation in which the sensing of the hydrogen is required. In this case, when the several sensors according to the present invention are used, the hydrogen sensing performance may be more improved.

Although the specific embodiments are described in the detailed description of the present invention, various changes may be made without departing from the scope of the present invention. Therefore, the scope of the present invention is not intended to be limited to the specific embodiments set forth above, but should be defined by the appended claims and their equivalents of the present invention, which are described later.

INDUSTRIAL APPLICABILITY

The present invention relates to a sensor, and more particularly, to a sensor capable of sensing hydrogen at a low cost.

The invention claimed is:

1. A sensor comprising:
a core which reacts with hydrogen to change in resistance value;
at least two electrodes connected to the core; and
a variable resistor connected to one of the at least two electrodes and having a resistance value that changes in response to a control signal,
wherein the core includes,
a first palladium layer having a contiguous thin film shape, and
a plurality of graphene layers printed on the palladium and having a contiguous thin film shape,
wherein a number of layers of graphene is greater than a number of layers of palladium, wherein the plurality of graphene layers includes, a first graphene layer printed on the first palladium layer, a second graphene layer printed on the first graphene layer, and a third graphene layer printed directly on the second graphene layer.

2. The sensor of claim 1, wherein a sum of thickness of layers of graphene is greater by N times that of the palladium (where N is a natural number).

3. The sensor of claim 2, where N has a value of 7.

4. The sensor of claim 2, wherein the variable resistor applies an offset resistance value to a variation in resistance value of the core in response to the control signal.

5. The sensor of claim 2, wherein N has a value of greater than or equal to 2 and less than or equal to 9.

6. The sensor of claim 1, further comprising:
a housing for protecting the core and the at least two electrodes; and
a fixing member inserted into the housing, the fixing member fixing the core and the at least two electrodes, the fixing member contacting the palladium and the graphene.

7. The sensor of claim 6, wherein the fixing member includes cotton.

8. The sensor of claim 6, wherein the variable resistor is connected through the housing.

9. The sensor of claim 1, wherein the core has a fan shape or a circular shape.

10. The sensor of claim 1, wherein, in response to the control signal, the variable resistor is set to a resistance value of 0 kilo-ohms to about 10 kilo-ohms.

11. The sensor of claim 1, wherein the core has a thickness of 10 millimeters or less.

12. A sensor comprising:
a core which reacts with hydrogen to change in resistance value;
at least two electrodes connected to the core;
a variable resistor connected to one of the at least two electrodes and having a resistance value that changes in response to a control signal; and
a housing that protects the core and the at least two electrodes and having an opening to connect the one of the at least two electrodes to the variable resistor,
wherein the core includes,
a single palladium layer having a thin film shape, and
a plurality of graphene layers printed on the palladium and having a thin film shape, wherein the plurality of graphene layers includes, a first graphene layer printed on the single palladium layer, a second graphene layer printed on the first graphene layer, and a third graphene layer printed directly on the second graphene layer.

13. A sensor comprising:
a core which reacts with hydrogen to change in resistance value;
at least two electrodes connected to the core; and
a variable resistor connected to one of the at least two electrodes and having a resistance value that changes in response to a control signal,
wherein the core consists of,
a single layer of palladium having a thin film shape,
a first layer of graphene printed on the palladium and having a thin film shape, and
second to Nth layers of graphene printed on respective ones of the first to (N−1)th layer of graphene (where N is a natural number).

* * * * *